United States Patent
Wunderer et al.

(10) Patent No.: US 6,595,060 B2
(45) Date of Patent: Jul. 22, 2003

(54) METHOD FOR DETERMINING STRUCTURAL INHOMOGENEITIES IN SHEET MATERIAL

(75) Inventors: Bernd Wunderer, Munich (DE); Ulrich Schanda, Holzkirchen (DE)

(73) Assignee: Giesecke & Devrient GmbH (DE)

( * ) Notice: Subject to any disclaimer, the term of this patent is extended or adjusted under 35 U.S.C. 154(b) by 0 days.

(21) Appl. No.: 09/885,120

(22) Filed: Jun. 21, 2001

(65) Prior Publication Data

US 2002/0014120 A1 Feb. 7, 2002

(30) Foreign Application Priority Data

Jun. 21, 2000 (DE) .......................................... 100 29 442

(51) Int. Cl.⁷ .............................................. G01N 29/04
(52) U.S. Cl. ............................ 73/597; 73/159; 73/598; 73/602
(58) Field of Search ...................... 73/597, 159, 573, 73/598, 627, 644, 602; 367/152

(56) References Cited

U.S. PATENT DOCUMENTS

| | | | |
|---|---|---|---|
| 4,446,735 A | 5/1984 | Weilacher | 73/597 |
| 4,612,807 A | 9/1986 | Wunderer | 73/580 |
| 4,730,495 A * | 3/1988 | Green | 73/620 |
| 4,976,150 A * | 12/1990 | Deka | 73/644 |
| 5,398,538 A | 3/1995 | Williams et al. | |
| 5,476,011 A * | 12/1995 | Cornforth | 73/641 |
| 5,493,911 A | 2/1996 | Hall et al. | 73/597 |
| 5,691,474 A | 11/1997 | Gerz | 73/580 |
| 5,922,957 A * | 7/1999 | Chatellier et al. | 73/580 |
| 5,922,960 A * | 7/1999 | Toda | 73/597 |
| 5,938,334 A | 8/1999 | Kayani | 374/44 |
| 5,986,457 A | 11/1999 | Kayani | 324/671 |
| 6,359,446 B1 * | 3/2002 | Little, Jr. | 324/637 |
| 6,407,964 B1 * | 6/2002 | Hornung et al. | 367/138 |

FOREIGN PATENT DOCUMENTS

| | | |
|---|---|---|
| DE | 30 48 710 | 7/1982 |
| DE | 34 24 652 | 1/1986 |
| DE | 44 46 367 | 6/1996 |
| DE | 198 44 447 | 3/2000 |
| EP | 0318229 | 5/1989 |
| JP | 5005780 | 1/1993 |

* cited by examiner

*Primary Examiner*—Helen Kwok
*Assistant Examiner*—Jacques Saint-Surin
(74) *Attorney, Agent, or Firm*—Bacon & Thomas, PLLC

(57) ABSTRACT

A method for determining structural inhomogeneities in sheet material including exposing sheet material to ultrasonic waves, measuring ultrasonic waves transmitted through the sheet material and ultrasonic waves reflected from the sheet material at a plurality of predetermined portions located linearly along at least one track disposed on the sheet material and producing at least one value characteristic based on at least the transmitted or reflected ultrasonic waves from each of the predetermined portions on the at least one track. The method further includes forming a first mean based on the at least one value characteristic and a second mean based on the first mean to determine the structural inhomogeneities in the sheet material representative of the at least one track.

6 Claims, 1 Drawing Sheet

METHOD FOR DETERMINING STRUCTURAL INHOMOGENEITIES IN SHEET MATERIAL

BACKGROUND OF THE INVENTION

1. Field of Art

This invention relates to a method for determining structural inhomogeneities, in particular due to creases or tears, in sheet material such as bank notes.

2. Summary of the Prior Art

In the testing and sorting of bank notes, for example in commercial or central banks, one generally also determines the condition thereof, e.g. the degree of soiling. The bank notes are sorted according to their condition and handled differently in accordance therewith. While bank notes in bad condition are generally withheld and possibly destroyed, bank notes in good condition can be put back in circulation.

Besides soiling one can also use, for instance, structural inhomogeneities such as creases, fine tears or small holes in the bank note for assessing the condition thereof. Structural inhomogeneities in bank notes are measured using, for instance, optical methods by which the bank note to be tested is for example irradiated with light and the reflected or transmitted light fraction measured and evaluated. However, optical methods generally have the disadvantage that measurements can be easily disturbed by ambient light and the sensitivity of the usually employed detectors and the strength of the applied light sources are generally subject to time fluctuations which likewise falsify measurement. In addition, one often requires an imaging optic comprising lenses and/or apertures resulting in a certain adjustment effort in the production and maintenance of such measuring systems.

SUMMARY OF THE INVENTION

The invention is based on the problem of providing a method for determining structural inhomogeneities in sheet material which avoids the above disadvantages.

This problem is solved by exposing the sheet material to ultrasound and the ultrasound transmitted through the sheet material and/or reflected on the sheet material is measured, thereby producing at least a first value characteristic of the transmitted and/or reflected ultrasound. From the produced first value one then determines a measure of the structural inhomogeneities in the sheet material. The use of ultrasound avoids the influence of disturbances, in particular due to ambient light. In addition, it reduces the adjustment effort.

In a preferred embodiment of the method it is provided that the transmitted and/or reflected ultrasound is measured at a plurality of places on the sheet material and for each of the places where the transmitted or reflected ultrasound is measured one produces a first value characteristic of the transmitted or reflected ultrasound. From the first values or from second values formed from the first values one finally forms a first mean as a measure of the structural inhomogeneities in the sheet material. The first mean may be the arithmetic, geometric or quadratic mean of the first or second values. One thus determines an average measure of the structural inhomogeneities in the sheet material so that relatively great local fluctuations are compensated and thus a statement can be made about the condition of the sheet "altogether" with respect to creases or tears.

In another variant of the method, the first mean corresponds to the standard deviation of the first or second values from the arithmetic mean formed from the first or second values. The first mean then states the average deviation of the first or second values from their arithmetic mean and constitutes a measure of deviations of the structural inhomogeneities determined at the individual places from their average value.

In another embodiment of the method it is provided that the places where the transmitted and/or reflected ultrasound is measured are located on a track extending linearly on the sheet material. Preferably the places measured on the sheet material touch or overlap each other so as to define an interconnected track. The position and/or length and/or width of the track can be selected such that the track is not located in the area of elements additionally incorporated in or applied to the sheet material, in particular security threads, watermarks or hologram foils. This ensures that the first mean comes only from structural inhomogeneities in the sheet material itself and is not falsified by additional elements such as security threads.

Furthermore it is advantageous if the ultrasound transmitted through the sheet material and/or reflected on the sheet material is measured along a plurality of tracks in the sheet material, a first mean being formed from the first or second values for each track. From the thus obtained first means of the particular tracks one forms a second, for example arithmetic, geometric or quadratic mean as a measure of the structural inhomogeneities in the sheet material. This further averaging obtains an especially reliable statement about the structural inhomogeneities found in the sheet material on the average.

In another embodiment of the inventive method it is provided that the second values are formed from the second-order derivative of the first values. Thus causes contributions of structural inhomogeneities with greater spatial extent to be attenuated more greatly than contributions of smaller inhomogeneities. The first mean formed therefrom then takes more account of smaller structural inhomogeneities than larger ones, thereby permitting more precise statements about any existing smaller structural defects, e.g. small tears or folds.

DESCRIPTION OF THE DRAWINGS

The invention will now be explained in more detail with reference to figures, in which.

DETAILED DESCRIPTION OF THE INVENTION

Figure 1:
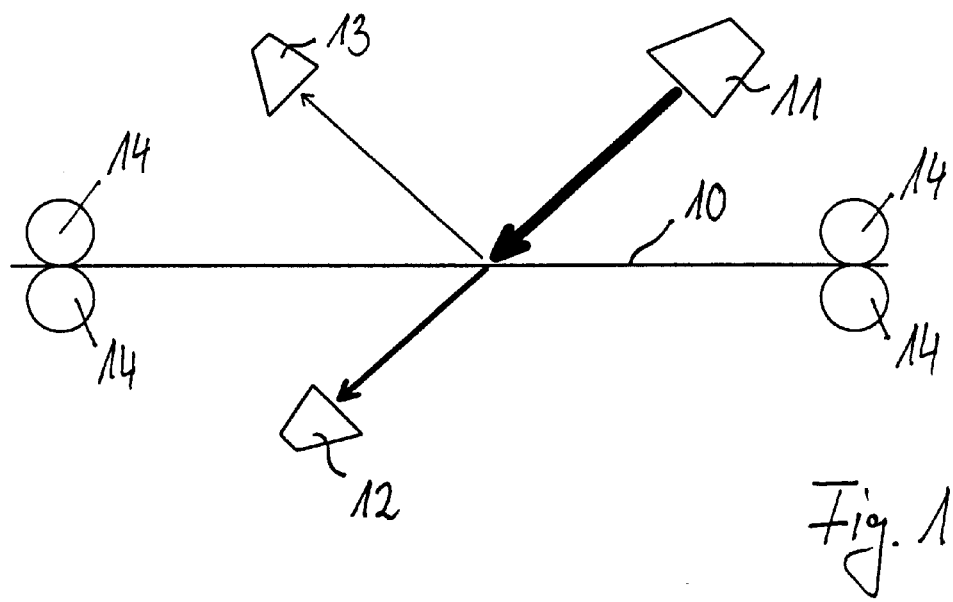
FIG. 1 shows an apparatus for caring out the inventive method.

FIG. 1 shows an apparatus for carrying out the inventive method. Sheet material 10 to be tested is transported between ultrasound transmitter 11 and ultrasound detector 12 with the aid of a transport device merely suggested here by transport rolls 14. The sound emitted by transmitter 11 and partially transmitted by sheet material 10 is detected by detector 12. Additionally or alternatively, partially reflected ultrasound can be detected by another ultrasound detector 13, as shown in the figure. To avoid spurious signals coming from a possible reflection of sound fractions between transmitter 11 and detector 12, 13, one disposes transmitter 11, sheet material 10 and detector 12, 13 obliquely to one other so that such reflections are removed from the beam path between transmitter 11 and detector 12, 13. As shown in the example, sheet material 10 is thus exposed to ultrasound at an angle other than 90°. Spurious signals can moreover also be eliminated if the sound propagation between transmitter 11 and detector 12, 13 is determined and during actual measurement detector 12, 13 is switched on with a delay equal to the sound propagation and switched off again at the end of two times the sound propagation at the latest.

The reflection and/or transmission behavior of sheet material 10 is preferably determined at a plurality of places on sheet material 10, in particular places located on a track extending linearly on the sheet material. The individual places on a track may partially overlap or touch each other or also be spaced certain distances apart. A track measurement is realized for example by transporting sheet material 10 past ultrasound detectors 12, 13, in particular at constant speed, and measuring the reflected and/or transmitted sound at certain time intervals. Another way of realizing a track measurement may be to measure the reflected and/or transmitted ultrasound with a plurality of ultrasound detectors disposed in a row (not shown), each ultrasound detector corresponding to an individual place on sheet material 10.

Figure 2:
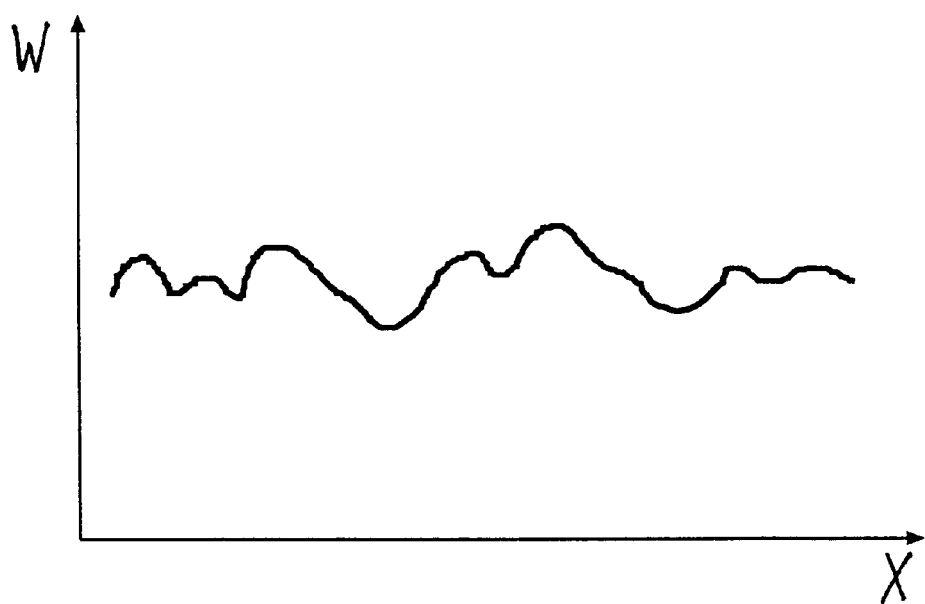
FIG. 2 shows a graphic representation of first values determined on a track extending linearly on the sheet material.

FIG. 2 shows a diagram with first values determined on a track extending linearly on the sheet material. First values W are plotted over particular places X on the sheet material. The shown case involves a measurement whereby individual places X where first values W are determined are located close together. According to the invention one forms from this graphic curve of discrete first values the first mean as a measure of the structural inhomogeneities in the sheet material. The first mean can be e.g. the arithmetic, geometric or quadratic mean or also the standard deviation of the measured values from the arithmetic mean. By forming the second-order derivative of this graphic curve of first values W according to places X, i.e. the place on sheet material 10, one produces second values (not shown) in an alternative variant of the method. Forming the second-order derivative causes contributions of structural inhomogeneities of greater extent to be attenuated more greatly than contributions of smaller structural inhomogeneities. If the first mean is formed from the thus produced second values it takes more account of smaller structural inhomogeneities, thereby permitting in particular statements about the presence of smaller creases or other structural fluctuations.

If required it may be provided that the tested sheet material is supplied to a device for smoothing creases, for example a suitable ironing device, in dependence on the calculated first or second mean. After being smoothed the bank notes can then be put back in circulation, possibly after another determination of any remaining structural inhomogeneities.

What is claimed is:

1. A method for determining structural inhomogeneities in sheet material, the method comprising steps of:

exposing sheet material to ultrasonic waves;

measuring ultrasonic waves transmitted through the sheet material and/or ultrasonic waves reflected from the sheet material at a plurality of predetermined portions located linearly along at least one track disposed on the sheet material;

producing at least one value characteristic based on at least the transmitted and/or reflected ultrasonic waves from each of the predetermined portions on the at least one track;

forming a first mean based on the at least one value characteristic; and forming a second mean based on the first mean to determine the structural inhomogeneities in the sheet material representative of the at least one track.

2. The method of claim 1, further comprising steps of:

determining an arithmetic mean from first and second values of the at least one value characteristic measured from each portion along the at least one track;

determining the standard deviation from the arithmetic mean; and assigning the arithmetic mean as the first mean.

3. The method of claim 2, wherein the second value characteristics are formed by the second-order derivative of the first value characteristics.

4. The method of claim 1, wherein a position, length and/or width of the at least one track disposed on the sheet material is located in at least one area of the sheet material free of elements additionally incorporated in or applied onto the sheet material.

5. The method of claim 1, wherein the second mean is formed by quadratic averaging of the first mean.

6. The method of claim 1, wherein the sheet material is transported to an ironing device for smoothing the structural inhomogenities operable in accordance with the first and second mean.

* * * * *